United States Patent [19]

Ishikura

[11] Patent Number: 4,620,003
[45] Date of Patent: Oct. 28, 1986

[54] PROCESS FOR PRODUCING 2-QUINOXALINOLS

[75] Inventor: Tsukasa Ishikura, Ageo, Japan

[73] Assignee: Nippon Kayaku Kabushiki Kaisha, Tokyo, Japan

[21] Appl. No.: 611,969

[22] Filed: May 18, 1984

[30] Foreign Application Priority Data

May 25, 1983 [JP] Japan .................................. 58-90771

[51] Int. Cl.⁴ ........................ C07D 241/44; C07B 1/00
[52] U.S. Cl. .................................................. 544/354
[58] Field of Search ........................................ 544/354

[56] References Cited

PUBLICATIONS

Moore et al. J. Org. Chem. 23, 1504 (1958).
Elina I, Chem. Abs. 59, 12807(c).
Elina II, Chem. Abs. 52, 20186(f).
Elina III, Chem. Abs. 58, 9059(e).
Fusco et al, Chemical Abstract, vol. 61, 4352b (1964).

*Primary Examiner*—Mark L. Berch
*Attorney, Agent, or Firm*—Cushman, Darby & Cushman

[57] ABSTRACT

The present invention relates to a process for preparing a 2-quinoxalinol compound, in the free form, of the following formula (II);

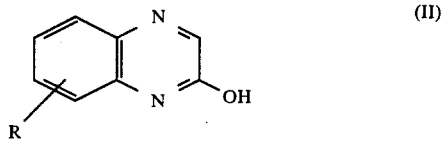

wherein R is hydrogen, halogen or a trifluoromethyl group, which comprises reducing a 2-quinoxalinol-4-oxide compound, in the free form, of the following formula (I);

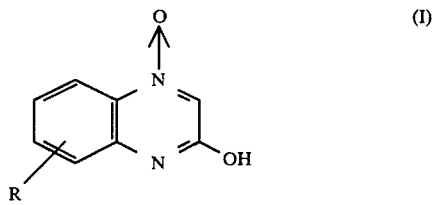

wherein R is a defined above, with hydrazine in the presence of a Raney catalyst and a hydroxide of an alkali metal or an alkaline earth metal or ammonium hydroxide.

7 Claims, No Drawings

PROCESS FOR PRODUCING 2-QUINOXALINOLS

The present invention relates to a process for producing a 2-quinoxalinol compound, and more particularly to a process for producing a 2-quinoxalinol compound, in the free form, of the following formula (II);

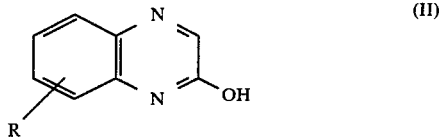

wherein R is hydrogen, halogen or a trifluoromethyl group, which comprises reducing a 2-quinoxalinol-4-oxide compound, in the free form, of the following formula (I);

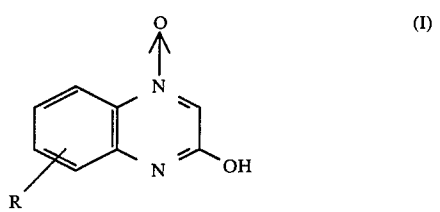

wherein R is as defined above, with hydrazine in the presence of a Raney catalyst and a hydroxide of an alkali metal or an alkaline earth metal or ammonium hydroxide.

2-Quinoxalinols are very useful as intermediates for the production of pharmaceuticals and agrochemicals.

Some of methods for producing the 2-quinoxalinol compounds of formula (II) from the 2-quinoxalinol-4-oxide compounds of formula (I) by reduction are reported as follows.

In Chemical Abstracts Vol. 61, 4352b (1964), the reduction is carried out at 180° C. with triphenylphosphine. This method is industrially disadvantageous in that an expensive reagent (triphenylphosphine) is used and the reaction is carried out at a high temperature. Japanese Patent Laid-Open No. 37791/1975 discloses a method wherein the reduction of 2-quinoxalinol-4-oxide compounds is carried out in the presence of an acid with iron, zinc, tin, triphenylphosphine, sodium arsenite, ammonium sulfide or sodium dithionite. This method gives the purpose compounds in very low yield since the 2-quinoxalinol-4-oxide compounds are unstable under acidic conditions. Japanese Patent Laid-Open No. 48973/1982 discloses a method wherein the reduction of 2-quinoxalinol-4-oxide compounds is carried out with zinc, iron or tin in an aqueous alkaline solution. This method requires costly steps of separating the purpose compounds from their metal oxides as by-products and aftertreating the separated metal oxides, and the yield of the purpose compounds is as low as 75 to 78%. Thus, this method is industrially disadvantageous. Japanese Patent Laid-Open No. 188575/1982 discloses a method wherein the reduction of 2-quinoxalinol-4-oxide compounds is carried out with sodium borohydride in an aqueous alkaline solution. This method is industrially disadvantageous in that an expensive reagent (sodium borohydride) is used. Japanese Patent Laid-Open No. 197270/1982 discloses a method wherein the reduction of 2-quinoxalinol-4-oxide compounds is carried out with a hydrogensulfite or a sulfite in an aqueous alkaline solution. This method is also industrially disadvantageous in that it requires a very costly step of aftertreating, the sulfite compounds used in an excess quantity after a reaction and the yield of the purpose compounds is as low as 72 to 86%.

The inventor has made studies to find out a method for producing 2-quinoxalinol compounds from 2-quinoxalinol-4-oxide compounds, which is inexpensive and free from disadvantages associated with the prior art methods, and has found that when a 2-quinoxalinol-4-oxide compound is reduced with hydrazine in the presence of a Raney catalyst and a hydroxide of an alkali metal or an alkaline earth metal or ammonium hydroxide, 2-quinoxalinol compounds can be obtained in high yield. The present invention is based on this finding.

The reaction of the present invention proceeds as follows:

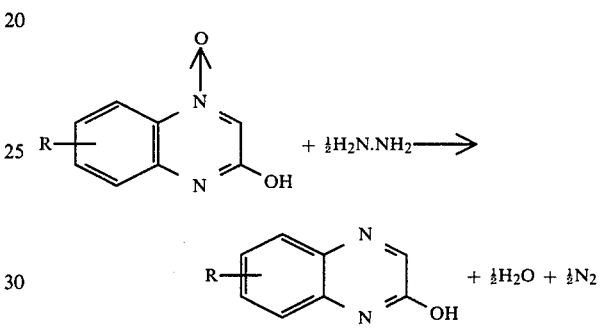

wherein R is as defined above.

Now the present invention will be described in more detail.

Examples of alkali metal and alkaline earth metal hydroxides to be used in the present invention include sodium hydroxide, potassium hydroxide, lithium hydroxide, calcium hydroxide, barium hydroxide, magnesium hydroxide or a mixture thereof. Among these compounds, sodium hydroxide and potassium hydroxide are particularly preferred. Ammonium hydroxide can be also used.

The hydroxides are used in a quantity of 1 to 20% by weight, preferably 3 to 15% by weight based on that of solvent to be used.

Examples of Raney catalysts used in the present invention include metals such as nickel, cobalt, copper, iron, palladium and mixtures thereof and a mixture thereof with small amounts of chromium, molybdenum, lead, manganese, cadmium or the like.

Among these catalysts, Raney nickel and Raney cobalt catalysts are particularly preferred. These Raney catalysts may be used also by immersing them in an aqueous solution of a sulfur compound such as a sulfite, an acid sulfite hydrosulfite, sodium sulfide, a sodium hydrosulfide, a sulfide and a thiol.

The Raney nickel catalyst treated with an aqueous acid sulfite solution is particularly preferred in respect of yield and quality of a purpose compound and the quantity of the catalyst to be used. As an acid sulfite, acid sodium sulfite or acid potassium sulfite is used. The catalyst is used in a quantity of 0.1 to 10% by weight based on that of starting materials, 2-quinoxalinol-4-oxide compounds.

Usually, hydrazine is used in the form of hydrate and in a quantity of 1.0 to 2.0 times as much as the theoretical quantity. Water is preferred as a reaction solvent but a solvent mixture of water and an organic solvent may also be used. The presence of acetate, cyanide, carbonate or the like existing in the starting material does not interfere with carrying out the reaction of the present invention. The reaction temperature is in the range of about 0° to 100° C. and preferably in the range of 40° to 80° C. The reaction time varies depending on the type of the catalyst, the reaction temperature, or the like, but is usually 10 min to 12 hr.

It is also possible to obtain the purpose compounds by treating the reaction mixture with an oxidizing agent such as hydrogen peroxide or activated carbon after the completion of the reaction to oxidize by-products excessively reduced.

After the completion of the reaction, the catalyst are removed from the reaction mixture and an aqueous alkaline solution containing 2-quinoxalinol compounds is neutralized with an acid such as hydrochloric acid and sulfuric acid to obtain the purpose products as crystals.

The following examples are provided to illustrate the present invention, but are not to be construed as limiting the present invention in any way.

EXAMPLE 1

An aqueous Raney nickel paste (containing 0.5 g of metallic nickel) and 5.0 g of a 80% aqueous hydrazine hydrate solution were added dropwise to 200 g of an aqueous solution containing 16.2 g of 2-quinoxalinol-4-oxide and 8 g of sodium hydroxide at a temperature of 40° to 50° C., and the resulting mixture was stirred at 40° to 70° C. for 5 hr, whereby the reducing reaction was terminated. The catalyst was then recovered by filtration, and 35% hydrochloric acid was added dropwise to the filtrate at 50° to 60° C. to adjust the pH to 4. The precipitated crystal was collected by filtration, washed with water and dried to give 13.4 g (yield 92%) of 2-quinoxalinol with melting point of 268° C.

EXAMPLE 2

An aqueous Raney nickel paste (containing 0.5 g of metallic nickel) and 5.0 g of a 80% aqueous hydrazine hydrate solution were added dropwise to 200 g of an aqueous solution containing 19.7 g of 6-chloro-2-quinoxalinol-4-oxide and 8 g of sodium hydroxide at 40° to 50° C., and the resulting mixture was stirred at 40° to 70° C. for 5 hr, whereby the reducing reaction was terminated. The catalyst was then recovered by filtration, and 35% hydrochloric acid was added dropwise to the filtrate at 50° to 60° C. to adjust the pH to 4. The precipitated crystal was collected by filtration, washed with water and dried to give 16.2 g (yield 90%) of 6-chloro-2-quinoxalinol with melting point of not lower than 300° C.

After the reaction was carried out in a similar manner to that described above, 3.0 g of a 35% aqueous hydrogen peroxide solution was added dropwise to the reaction mixture at 50° to 60° C. and the solution was treated for 20 min. The catalyst was then removed by filtration, and the filtrate was treated in a similar manner to that described above to give 16.8 g (yield 93%) of 6-chloro-2-quinoxalinol.

After the reaction was carried out in a similar manner to that described above, 2 g of activated carbon was added to the reaction mixture at 50° C. and the solution was treated for 20 min. The catalyst and activated carbon were then removed, and the pH of the filtrate was adjusted to 4 by adding 35% hydrochloric acid, giving 16.6 g (yield 92%) of 6-chloro-2-quinoxalinol.

EXAMPLE 3

An aqueous Raney nickel paste (containing 50 g of metallic nickel) was suspended in 200 g of water with stirring, and 50 g of a 15% aqueous acid sodium sulfite solution was added dropwise thereto. The mixture was stirred at 20° to 30° C. for one hr to obtain a treated catalyst (I).

The treated catalyst (I) (containing 0.3 g of metallic nickel) and 4.0 g of a 80% aqueous hydrazine hydrate solution were added dropwise to 240 g of an aqueous solution containing 19.7 g of 6-chloro-2-quinoxalinol-4-oxide and 28 g of potassium hydroxide at 40° to 50° C., and the reaction was carried out at 40° to 80° C. for 5 hr. After the catalyst was removed, the filtrate was acidified to give 17.3 g (yield 96%) of 6-chloro-2-quinoxalinol.

EXAMPLE 4

The treated catalyst (I) (containing 0.3 g of metallic nickel) and 4.0 g of a 80% aqueous hydrazine hydrate solution were added dropwise to 300 g of an aqueous solution containing 23.0 g of 6-trifluoromethyl-2-quinoxalinol-4-oxide and 8 g of sodium hydroxide at 40° to 50° C., and the reaction was carried out at 40° to 80° C. for 5 hr. After the catalyst was removed by filtration, the filtrate was acidified to give 20.1 g (yield 94%) of 6-trifluoromethyl-2-quinoxalinol with melting point of 260° C.

EXAMPLE 5

The procedure of Example 2 was repeated except that an aqueous Raney cobalt paste (containing 0.5 g of metallic cobalt) was used in place of the Raney nickel paste. 15.7 g (yield 87%) of 6-chloro-2-quinoxalinol was obtained. (The hydrogen peroxide treatment and activated carbon treatment were not carried out.)

EXAMPLE 6

The procedure of Example 3 was repeated except that 29 g of magnesium hydroxide was used in place of the potassium hydroxide. 15.8 g (yield 88%) of 6-chloro-2-quinoxalinol was obtained.

EXAMPLE 7

The procedure of Example 3 was repeated except that 60.3 g of a 29% aqueous ammonium hydroxide solution was used in place of the potassium hydroxide. 16.0 g (yield 89%) of 6-chloro-2-quinoxalinol was obtained.

What I claim is:

1. A process for preparing a 2-quinoxalinol compound of the formula:

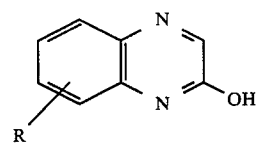

in which R is hydrogen, halogen or a trifluoromethyl group, which comprises reducing a 2-quinoxalinol-4-oxide compound of the formula:

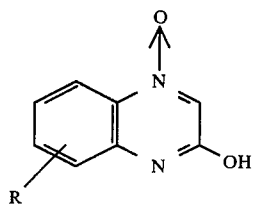

where R is as defined above, with hydrazine in the presence of a Raney catalyst and an alkali metal hydroxide, an alkaline earth metal hydroxide, or ammonium hydroxide.

2. The process according to claim 1 in which the Raney catalyst is treated with an aqueous solution of a sulfite, an acid sulfite, or a hydrosulfite.

3. The process according to claim 2 in which the Raney catalyst is Raney nickel treated with an aqueous acid sulfite solution.

4. The process according to claim 3 in which the reaction is conducted in the presence of sodium hydroxide.

5. The process according to claim 4 in which the reaction is carried out at a temperature of from 40° to 80° C.

6. The process according to claim 3 in which the reaction is conducted in the presence of potassium hydroxide.

7. The process according to claim 6 in which the reaction is carried out at a temperature of from 40° to 80° C.

* * * * *